(12) United States Patent
Tsuji

(10) Patent No.: US 7,119,737 B2
(45) Date of Patent: Oct. 10, 2006

(54) MICROWAVE SENSOR

(75) Inventor: Masatoshi Tsuji, Ohtsu (JP)

(73) Assignee: OPTEX Co., Ltd., Shiga (JP)

( * ) Notice: Subject to any disclaimer, the term of this patent is extended or adjusted under 35 U.S.C. 154(b) by 284 days.

(21) Appl. No.: 10/493,018

(22) PCT Filed: Oct. 21, 2002

(86) PCT No.: PCT/JP02/10899

§ 371 (c)(1),
(2), (4) Date: Apr. 19, 2004

(87) PCT Pub. No.: WO03/036326

PCT Pub. Date: May 1, 2003

(65) Prior Publication Data

US 2004/0246166 A1  Dec. 9, 2004

(30) Foreign Application Priority Data

Oct. 19, 2001  (JP) .............................. 2001-321704

(51) Int. Cl.
*G01S 13/04* (2006.01)
*G08B 13/18* (2006.01)

(52) U.S. Cl. .................. 342/129; 342/27; 342/127; 340/552

(58) Field of Classification Search .............. 342/27, 342/28, 127, 129; 340/552
See application file for complete search history.

(56) References Cited

U.S. PATENT DOCUMENTS

| | | | |
|---|---|---|---|
| 3,750,171 A | | 7/1973 | Faris |
| 3,832,709 A | * | 8/1974 | Klein et al. ............... 342/127 |
| 3,952,303 A | | 4/1976 | Watanabe et al. |
| 4,195,289 A | * | 3/1980 | Cole ......................... 340/554 |
| 5,923,284 A | | 7/1999 | Artis et al. |
| 6,703,967 B1 | * | 3/2004 | Kuroda et al. .............. 342/129 |

FOREIGN PATENT DOCUMENTS

| | | |
|---|---|---|
| JP | 49-107491 | 10/1974 |
| JP | 1-285884 | 11/1989 |
| JP | 7-37176 | 2/1995 |
| JP | 10-39009 | 2/1998 |
| JP | 10-197626 | 7/1998 |
| JP | 10-200429 | 7/1998 |
| JP | 11-183602 | 7/1999 |
| JP | 2002-236162 | 8/2002 |
| JP | 2002-236163 | 8/2002 |
| JP | 2002-236173 | 8/2002 |

OTHER PUBLICATIONS

The Transaction of the Institute of Electronics, Information and Communication Engineers, vol. J72-BII, No. 9, Sep. 25, 1989, pp. 425-514.

* cited by examiner

*Primary Examiner*—Ian J. Lobo
(74) *Attorney, Agent, or Firm*—Wenderoth, Lind & Ponack, L.L.P.

(57) ABSTRACT

Actual correlation data is stored at 38A. Such actual correlation data is data representation(s) of correlation(s) between or among distance(s) to object(s) intended to be detected and phase difference(s) of respective reflected wave(s) established with due consideration having been given to reflection of microwave(s) by object(s) (ceiling surface(s), wall surface(s), floor surface(s), etc.) other than object(s) intended to be detected which may be present within area(s) intended to be protected. Distance(s) to object(s) intended to be detected is or are measured, based on such actual correlation data, from phase difference(s) of respective reflected wave(s) that has or have been detected.

4 Claims, 4 Drawing Sheets

(a)          (b)

Δt

MICROWAVE SENSOR

TECHNICAL FIELD

The present invention relates to a microwave sensor (hereinafter "MW sensor") which is an active sensor employing electromagnetic waves lower in frequency than visible light. In particular, the present invention relates to an improved MW sensor making use of a plurality of microwaves of different frequency to detect object(s).

BACKGROUND ART

Conventionally known as one security device is an MW sensor wherein microwaves are transmitted toward protected area(s), and, in the event that person(s) is or are present within protected area(s), wave(s) reflected from such person(s) (microwave(s) modulated due to the Doppler effect) are received and person(s) (intruder(s)) is or are detected (e.g., Japanese Patent Application Publication Kokai No. H7-37176 (1995)).

Moreover, also known as one type of MW sensor is a device which employs a plurality of microwaves of different frequency and which is constituted so as to permit measurement of distance(s) to object(s). In this type of sensor, microwaves of, for example, two different frequencies are transmitted toward protected area(s), and phase difference(s) between two IF signals based on respective reflected waves is or are detected. Correlation(s) exist between or among such phase difference(s) and distance(s) to target(s) (person(s) and/or other such object(s) intended to be detected), phase difference(s) tending to increase with increasing distance(s) to target(s). In other words, distance(s) to target(s) can be measured by calculating such phase difference(s). Below, operations for detection of phase difference(s) between/among IF signals in this type of sensor are described. Taking the case where IF signals based on waves produced by reflection of microwaves of two different frequencies are sinusoidal waves IFout1, IFout2 (having a phase difference corresponding to distance to target) as shown at FIG. 3 (a), rectangular waves A, B derived from these IF signals might respectively be as shown at FIG. 3 (b). It will, moreover, be possible to measure the distance to the target by detecting the phase difference between these rectangular waves A, B (the phase difference Δt at the rising edge portion of the rectangular waves in the drawing).

However, where this type of sensor is installed indoors, measurement errors may occur due to the influence of microwaves reflected by ceiling surface(s), wall surface(s), and/or floor surface(s). More specifically, for targets present at the extreme near side of the sensor range (e.g., on the order of 0 to 2 m) or targets present at locations relatively distant from the sensor (e.g., locations 8 m or more from the sensor), such measurement errors are small. However, for targets present at locations other than the foregoing (e.g., locations on the order of 3 to 7 m from the sensor), it is possible that measurement error will be large. The reason this is the case is described below.

Referring to FIG. 4 (a), description is first made with respect to a situation where the target is present at the extreme near side of the sensor range. Receiving antenna(s) for this type of sensor "a" are chosen such that directionality with respect to reception of reflected waves received from the front (reflected waves in horizontal direction(s) which are directed toward the left in the drawing) is high; and conversely, such that directionality with respect to reception of reflected waves from the side(s) and from regions therebelow (e.g., the reflected wave indicated by the alternating long and short chain line in the drawing) is low. For this reason, if target "b" is present at the extreme near side of the range of sensor "a", microwaves from sensor "a" will directly irradiate target "b", these will also be directly reflected therefrom onto sensor "a" (the irradiated wave and reflected wave indicated by solid lines in the drawing; reflected waves received in such fashion being hereinafter referred to as normally reflected waves), and the received reflected wave signal level will be high with respect thereto. In contrast thereto, the received signal level will be extremely low for signals received at sensor "a" after reflection by ceiling surface "c", floor surface "d", and so forth as indicated by alternating long and short chain lines in the drawing. For this reason, because the reflected waves forming the IF signal for measurement of distance to target "b" are for the most part made up of the normally reflected waves indicated by the solid lines in the drawing, there is almost no occurrence of measurement error.

Referring to FIG. 4 (b), description is next made with respect to a situation where target "b" is present at a location relatively distant from sensor "a". In such a situation, where irradiated waves are reflected by ceiling surface "c" or the like as indicated by the dashed line in the drawing, or where reflected waves are reflected by floor surface "d" or the like as indicated by the alternating long and short chain line in the drawing, the path taken by microwaves will be longer than the path taken by normally reflected waves (the path indicated by solid lines in the drawing). However, because the distance to target "b" is large, it is possible to hold the difference between the foregoing paths to a value at or below on the order of 10 percent as a fraction of the distance to this target "b". For example, taking a case where target "b" is present at a distance of 10 m from sensor "a", even if the difference between the foregoing paths is as much as 1 m it will still be possible to hold the error to values at or below 10 percent. For this reason, errors due to reflection of microwaves at ceiling surface "c" and floor surface "d" have almost no effect.

In contrast thereto, where, as shown at FIG. 4 (c), target "b" is located neither at the extreme near side of the range of sensor "a" nor at a far distance from sensor "a", reflected waves received at sensor "a" after reflection by floor surface "d" and so forth as indicated by alternating long and short chain lines in the drawing will be received from angles near the front of the antenna, and the received signal level of such signals will be relatively high. Furthermore, where irradiated waves are reflected by ceiling surface "c" or the like as indicated by the dashed line in the drawing or where reflected waves are reflected by floor surface "d" or the like as indicated by the alternating long and short chain line in the drawing, the path taken by microwaves is longer than the path taken by normally reflected waves. Because the distance from sensor "a" to target "b" is also relatively short it is possible that the difference between the foregoing paths could be large (e.g., on the order of 50 percent) as a fraction of the distance from this sensor "a" to target "b". In other words, reflected waves traveling via paths much longer than paths of normally reflected waves are received at sensor "a" with relatively high received signal levels. For this reason, IF signals being formed from waves representing superposition of the foregoing normally reflected waves and reflected waves traveling via paths longer than paths of such normally reflected waves, measurement errors arising due to the influence of the latter, i.e., reflected waves (reflected waves traveling via paths longer than paths of normally reflected waves) will increase, greatly impairing reliability of sensor "a".

Such problems are not limited to situations in which MW sensor(s) is or are installed indoors, but will also occur in similar fashion where MW sensor(s) is or are installed outdoors if object(s) constituting obstacle(s) is or are present within area(s) intended to be protected and microwaves are reflected by such object(s).

DISCLOSURE OF INVENTION

The present invention was conceived in light of the such points, it being an object thereof to provide, in an MW sensor employing a plurality of microwaves of different frequency to detect object(s), an MW sensor of high reliability capable of accurately measuring location(s) (distance(s) from sensor(s)) of target(s) notwithstanding the fact that such target(s) may be present at any location(s) within area(s) intended to be protected.

In order to achieve the foregoing object, the present invention prepares, as actual correlation data, correlation(s) between or among distance(s) to object(s) intended to be detected and phase difference(s) of respective reflected waves, such correlation(s) being with respect to actual and not theoretical values of both, with consideration having been given to reflection of respective microwave(s) irradiated from sensor(s) by object(s) other than object(s) (target(s)) intended to be detected, and carries out measurement of distance(s) to object(s) intended to be detected based on this actual correlation data.

More specifically, the present invention is predicated upon an MW sensor transmitting a plurality of microwaves of different frequency toward area(s) intended to be protected, and, in the event that object(s) intended to be detected is or are present within the area(s) intended to be protected, receiving respective microwave(s) which is or are reflected and measuring distance(s) to object(s) intended to be detected based on phase difference(s) between or among the reflected wave(s). This MW sensor is equipped with storage means and measuring means. Storage means stores or store, in advance as actual correlation data, correlation(s) between or among distance(s) to object(s) intended to be detected and phase difference(s) of respective reflected wave(s) established with due consideration having been given to reflection of microwave(s) by object(s) other than object(s) intended to be detected which may be present within area(s) intended to be protected. Measuring means measures or measure distance(s) to object(s) intended to be detected based on actual correlation data stored by such storage means.

In a specific example of installation of such an MW sensor, protected area(s) is or are space(s) within room(s); and object(s) other than object(s) intended to be detected are ceiling surface(s), wall surface(s), and/or floor surface(s).

As a result of such specific features, notwithstanding the fact that microwaves transmitted from sensor(s) toward area(s) intended to be protected may be reflected by object(s) (e.g., ceiling surface(s), wall surface(s), and/or floor surface(s)) other than object(s) intended to be detected and microwave path(s) may be longer than path(s) of the foregoing normally reflected wave(s), because the foregoing actual correlation data is prepared as data which takes into consideration portion(s) corresponding to such extension of path(s) due to reflection, it will be possible to obtain value(s) for distance(s) to object(s) intended to be detected as measured by sensor(s) that is or are in approximate agreement with actual distance(s) to object(s) intended to be detected.

In other words, even where object(s) that could produce reflected wave(s) other than normally reflected wave(s) is or are present within area(s) intended to be protected, it will nonetheless be possible to accurately measure distance(s) to object(s) intended to be detected and it will nonetheless be possible to achieve improved sensor reliability.

BEST MODE OF CARRYING OUT INVENTION

Below, embodiments of the present invention are described with reference to the drawings. Here, description is carried out in terms of a situation in which the present invention is applied to an MW sensor for use as a security sensor, the MW sensor being such that microwaves of two different frequencies are employed for measurement of distance(s) to target(s) (intruder(s) or the like).

Description of MW Sensor Constitution

Figure 1:
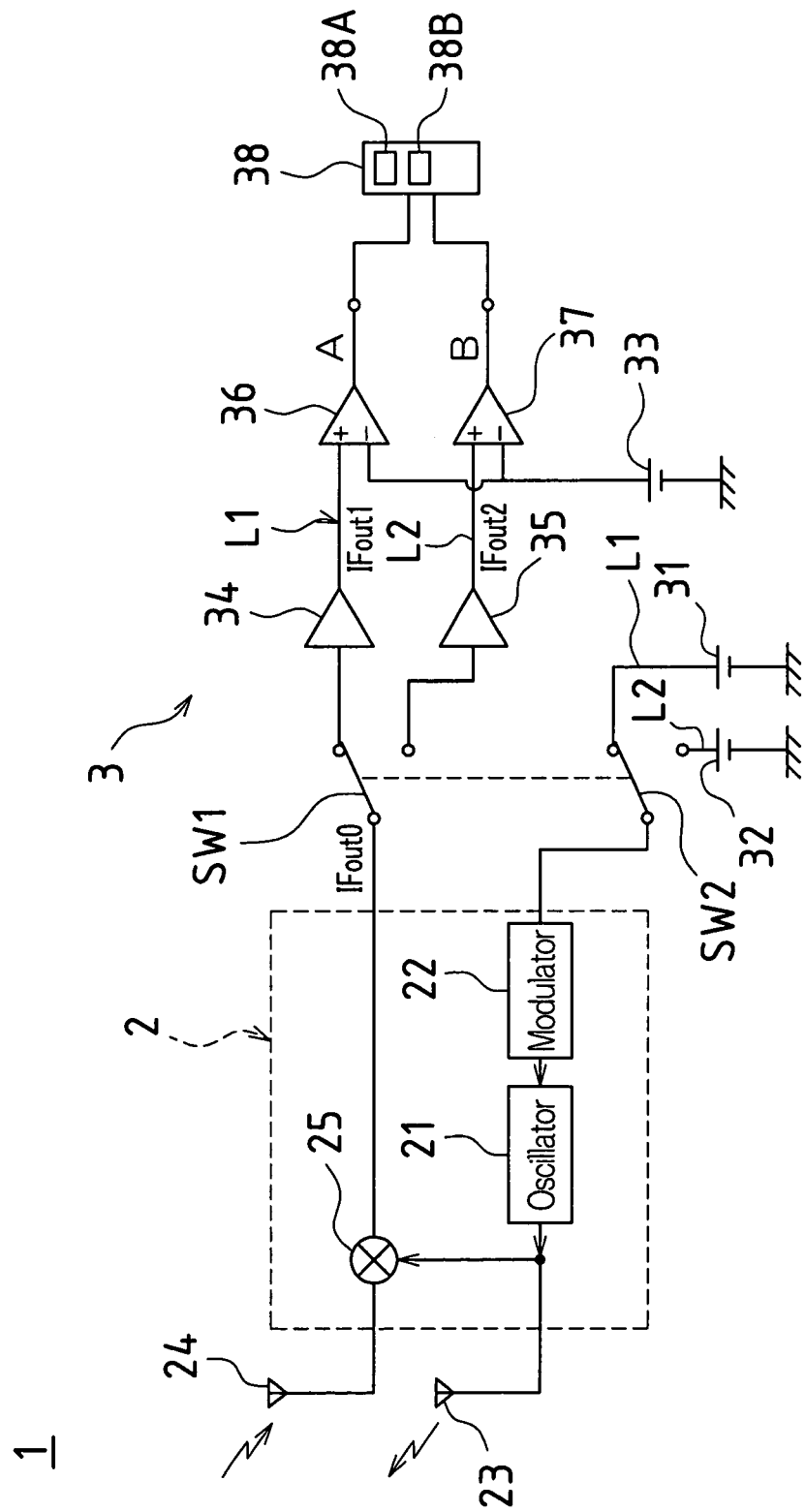
FIG. 1 is a drawing showing circuit structure in an MW sensor associated with an embodiment.

FIG. 1 shows circuit structure in an MW sensor 1 associated with the present embodiment. As shown in the drawing, MW sensor 1 is equipped with RF module(s) 2 and signal processing unit(s) 3.

RF module 2 is equipped with oscillator(s) 21 for generating microwaves, modulator(s) 22 for changing the frequency or frequencies of microwaves generated by such oscillator(s) 21, transmitting antenna(s) 23 for transmitting microwaves generated by oscillator(s) 21 toward protected area(s), receiving antenna(s) 24 for receiving microwaves reflected by person(s) or other such object(s), and mixer(s) 25 for mixing such received microwaves together with voltage waveform(s) from oscillator(s) 21 before output thereof. That is, in the event that there is or are person(s) or the like within protected area(s), microwaves transmitted toward protected area(s) from transmitting antenna(s) 23 will, upon reflection by such person(s) or the like, be modulated in frequency or frequencies due to the Doppler effect before being received by receiving antenna(s) 24. After being received, such reflected wave(s) are at mixer(s) 25 mixed with voltage waveform(s) from oscillator(s) 21 before being output as IF output signal(s) (IFout0) from RF module(s) 2 to signal processing unit(s) 3.

Furthermore, signal processing unit 3 is equipped with first output line(s) L1 and second output line(s) L2 respectively corresponding to each frequency of microwave transmitted from transmitting antenna(s) 23. Respective lines L1, L2 are equipped with power supplies 31, 32, 33, IF amplifiers 34, 35, and comparators 36, 37. A distance measuring arithmetic unit 38—which is characteristic of the present embodiment—is provided to the output side of comparators 36, 37.

Respective IF amplifiers 34, 35 are connected to the output side of RF module 2 by way of first switch SW1. First switch SW1 performs switching so as to cause connection to first output line L1 when one of the aforementioned two varieties of microwaves is transmitted from transmitting antenna 23, and so as to cause connection to second output line L2 when the other of the aforementioned two varieties of microwaves is transmitted from transmitting antenna 23. That is, the constitution here is such that IF output signal(s) (IFout1) associated with reflected wave(s) produced by reflection from person(s) or the like during transmission of one of the aforementioned two varieties of microwaves is or are output to first output line L1, and IF output signal(s) (IFout2) associated with reflected wave(s) produced by reflection from person(s) or the like during transmission of the other of the aforementioned two varieties of microwaves is or are output to second output line L2.

Furthermore, respective power supplies 31, 32 are connected to the input side of RF module 2 by way of second switch SW2 which works in linked fashion with the aforementioned first switch SW1. Switching of this second switch SW2 likewise causes connection to be made to either of respective power supplies 31, 32 depending on which of the aforementioned two varieties of microwaves is being transmitted from transmitting antenna 23. That is, the constitution here is such that modulator 22 is switched between two different microwave frequencies depending upon whether this second switch SW2 makes connection to the one power supply 31 or the other power supply 32, thus permitting the frequency of the microwaves transmitted from transmitting antenna 23 to be switched.

In accompaniment to switching operations occurring at respective switches SW1, SW2, switching thus occurs at regular time intervals (e.g., every several ms) between first processing operations wherein one of the aforementioned two varieties of microwaves is transmitted from transmitting antenna 23 toward protected area(s) and IF output signal(s) (IFout1) based on wave(s) produced by reflection thereof is or are output to first output line L1 of signal processing unit 3, with signal processing taking place at this first output line L1; and second processing operations wherein the other of the aforementioned two varieties of microwaves is transmitted from transmitting antenna 23 toward protected area(s) and IF output signal(s) (IFout2) based on wave(s) produced by reflection thereof is or are output to second output line L2 of signal processing unit 3, with signal processing taking place at this second output line L2. In addition, during the respective processing operations, IF output signals output from RF module 2 are amplified by IF amplifiers 34, 35, the outputs from such IF amplifiers 34, 35 being shaped into rectangular waves by comparators 36, 37 before being output to distance measuring arithmetic unit 38.

Moreover, describing the aforementioned respective processing operations in further detail, in the event that there is no person or the like within protected area(s), because frequency or frequencies of microwaves transmitted by transmitting antenna 23 will be equal to frequency or frequencies of microwaves received by receiving antenna 24, the IF frequencies of the signals output from IF amplifiers 34, 35 will be "0," and no signal will be output from comparators 36, 37. In contrast thereto, in the event that there is or are person(s) or other such object(s) within protected area(s), because microwaves received by receiving antenna 24 will be modulated relative to frequency or frequencies of microwaves transmitted by transmitting antenna 23, there will be a change in the output signal waveforms from comparators 36, 37, the rectangular waves therefrom being output to distance measuring arithmetic unit 38.

Description of Distance Measuring Arithmetic Unit 38

Distance measuring arithmetic unit 38, which receives output signal waveforms from comparators 36, 37, will next be described. This distance measuring arithmetic unit 38 receives output signal waveforms from the foregoing respective comparators 36, 37, measures distance(s) to object(s) (person(s)) intended to be detected based thereon, and outputs results of measurement.

Distance measuring arithmetic unit 38 is provided with storage means 38A and measuring means 38B. Description of the respective means follows below.

Figure 2:
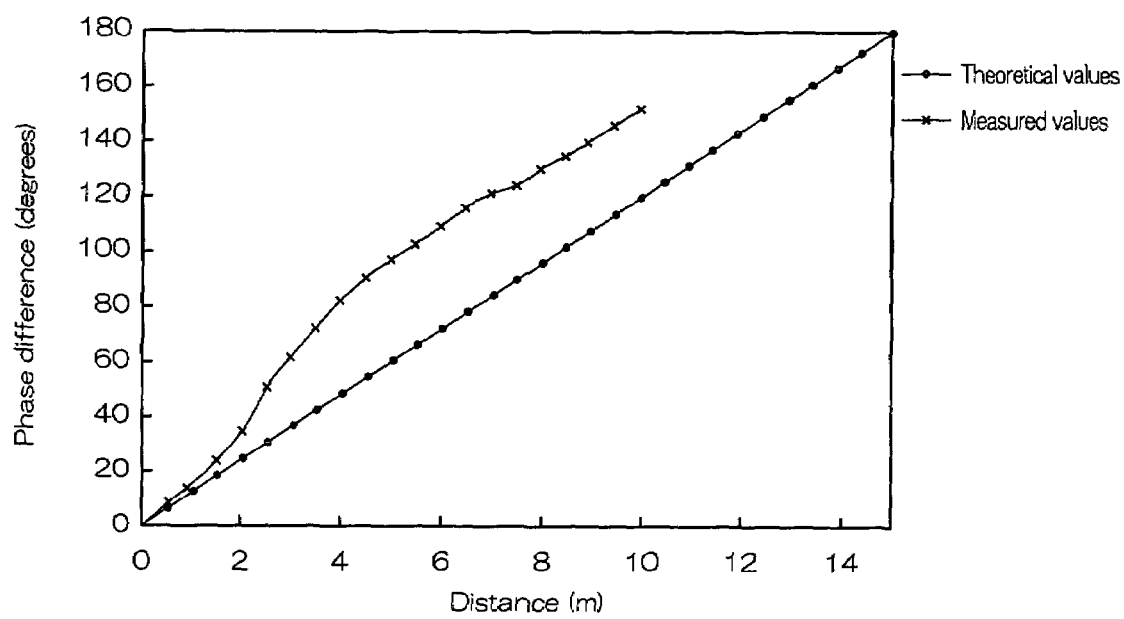
FIG. 2 is a drawing showing correlation between distance to target intended to be detected and phase difference of respective reflected waves.
Figure 3:
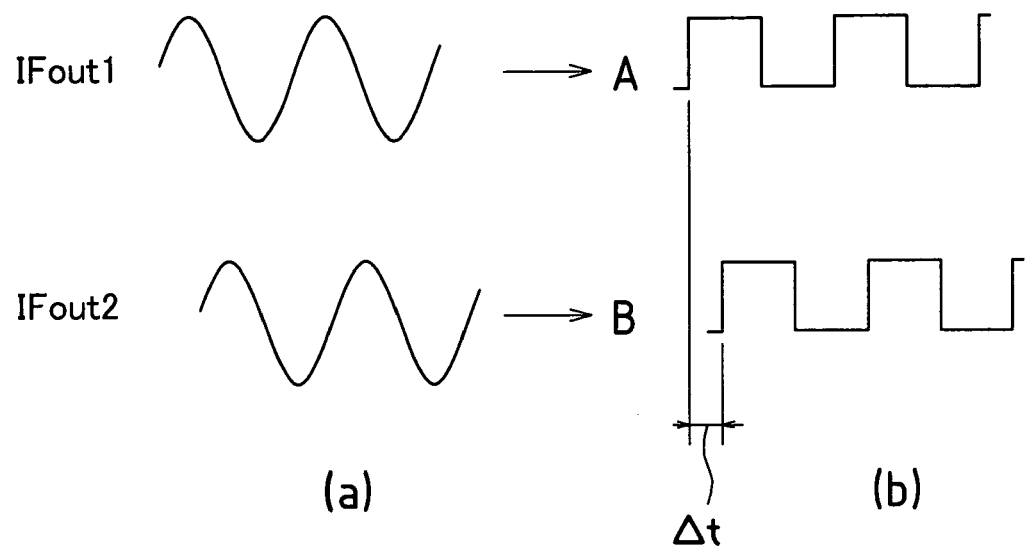
FIG. 3 is a drawing showing respective IF signals as well as rectangular waves which might be obtained therefrom in a conventional example.
Figure 4:
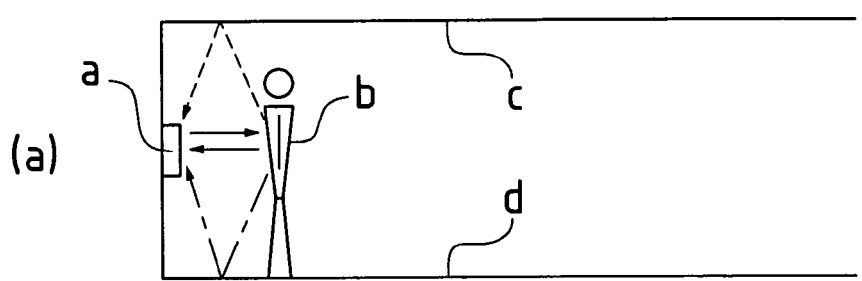
FIG. 4 contains drawings for explaining conventional problem(s); (a) at same FIG. being a drawing showing a situation in which a target is present at the extreme near side of the range of a sensor, (b) at same FIG. being a drawing showing a situation in which a target is present at a location relatively distant from a sensor, and (c) at same FIG. being a drawing showing a situation in which a target is present at a location approximately midway between that of (a) at same FIG. and that of (b) at same FIG.
Figure 4:
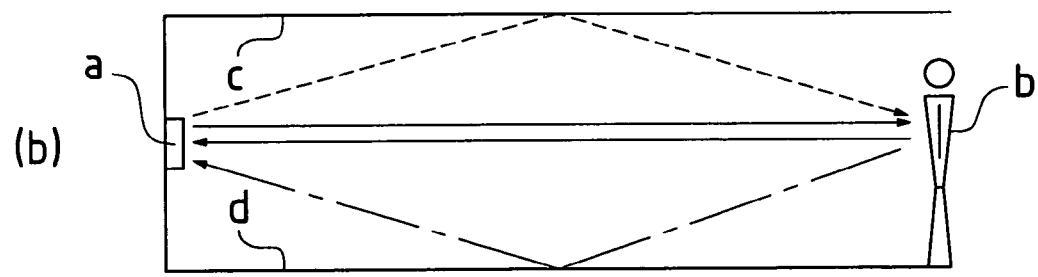
Figure 4:
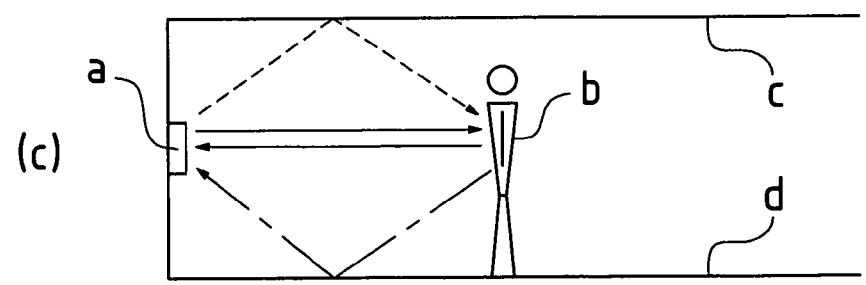

Storage means 38A stores, in advance as "actual correlation data," correlation(s) between or among distance(s) to object(s) intended to be detected and phase difference(s) of respective reflected wave(s) established with due consideration having been given to reflection of microwave(s) by ceiling surface(s), wall surface(s), and floor surface(s) constituting object(s) other than object(s) intended to be detected which may be present within area(s) intended to be protected. This "actual correlation data" is data established taking into account degree(s) to which correlations between or among distance(s) to object(s) intended to be detected and phase difference(s) of respective reflected waves will be shifted from theoretical value(s) as a result of reflection of microwave(s) by ceiling surface(s), wall surface(s), and floor surface(s) when such MW sensor(s) 1 is or are installed in room(s) of typical size(s). For example, as shown in FIG. 2, the distance to an object intended to be detected and the phase difference of respective reflected waves are theoretically related after the fashion of a direct proportion. In contrast thereto, the actual correlation therebetween is actually displaced from theoretical values after the fashion of the measured values shown in the drawing due to influence of microwaves reflected by ceiling surface(s), wall surface(s), and floor surface(s). Such real-life correlation is ascertained in advance through experimentation or the like, and this "actual correlation data (programmed line(s))" is or are stored in advance at storage means 38A.

Moreover, measuring means 38B measures distance(s) to object(s) intended to be detected based on "actual correlation data" stored by the foregoing storage means 38A. That is, the phase difference between respective rectangular waveforms output from the foregoing comparators 36, 37 is determined, and the distance corresponding to this phase difference is detected based on the foregoing "actual correlation data." As a result, measurement of distance(s) to object(s) intended to be detected with due consideration having been given to the influence of reflection of microwaves by ceiling surface(s), wall surface(s), and floor surface(s) is permitted. Taking the example shown in FIG. 2, if the phase difference between reflected waves (phase difference between IF output signals) is 60°, the theoretical value for the distance to an object intended to be detected might be 5 m. However, this value includes an error due to the influence of reflection of microwaves by ceiling surface(s) and/or the like. In the present embodiment, the actual distance to the object intended to be detected can be measured as 3 m based on "actual correlation data" which takes into account the influence of reflection of microwaves by such ceiling surface(s) and/or the like.

As described above, the present embodiment permits measurement of distance(s) to object(s) intended to be detected based on "actual correlation data" established with due consideration having been given to reflection of microwaves by ceiling surface(s), wall surface(s), and floor surface(s). For this reason, notwithstanding the fact that microwaves transmitted toward area(s) intended to be protected may be reflected by ceiling surface(s) and/or the like and microwave path(s) may be longer than path(s) of the foregoing normally reflected wave(s), because the foregoing "actual correlation data" is prepared as data which preemptively takes into consideration portion(s) corresponding to such extension of path(s) due to reflection, it will be possible to obtain value(s) for distance(s) to object(s) intended to be detected as measured by sensor(s) that is or are in approximate agreement with actual distance(s) to object(s) intended to be detected. It is consequently possible to provide an MW sensor 1 of high reliability that is capable of accurately measuring distance(s) to object(s) intended to be detected.

OTHER EMBODIMENTS

The foregoing embodiment has been described in terms of an MW sensor 1 employing microwaves of two different frequencies to measure distance(s) to object(s) intended to be detected. The present invention is, however, not limited thereto, it being possible to employ microwaves of three or more different frequencies to measure distance(s) to object(s) intended to be detected.

Furthermore, the foregoing embodiment was described in terms of a situation in which an MW sensor 1 is installed indoors. The present invention is, however, not limited to thereto, it being possible to apply the present invention to an MW sensor that is installed outdoors. In such case, the foregoing "actual correlation data" would be prepared as data taking into account reflection of microwaves by obstacle(s) and/or the like within outdoor area(s) intended to be protected. Furthermore, a constitution may be adopted in which a single MW sensor is furnished with both "actual correlation data" corresponding to indoors and "actual correlation data" corresponding to outdoors, operation of a switch or the like causing switching of the "actual correlation data" to be used for measurement operations. Moreover, where furnished with a plurality of sets of "actual correlation data," a plurality of sets of "indoor actual correlation data" corresponding to indoor space sizes may be stored by storage means 38A and/or a plurality of sets of "outdoor actual correlation data" corresponding to arrangements and/or the like of obstacle(s) and/or the like in outdoor space(s) may be stored by storage means 38A.

Furthermore, the MW sensor 1 of the present invention may be employed in applications other than security sensors.

As described above, microwave sensor(s) in accordance with the present invention excel with respect to ability to accurately measure location(s) of object(s) intended to be detected notwithstanding the fact that such object(s) may be present at any location(s) within area(s) intended to be protected and may be effectively employed as highly reliable MW sensor(s).

The invention claimed is:

1. A microwave sensor operable to transmit a plurality of microwaves of different frequency toward an area intended to be protected, to receive respective reflected microwaves from an object to be detected if present within the area to be protected, and to measure the distance to the object to be detected based on phase difference between or among the reflected microwaves, wherein said microwave sensor includes: a storage means for storing in advance actual correlation data of actual correlations between or among distances to objects to be detected and phase differences of respective reflected waves that have been established based on microwave reflection by objects present within the area to be protected other than the objects to be detected; and a measuring means for measuring distances to objects to be detected based on the actual correlation data stored by said storage means.

2. The microwave sensor of claim 1, wherein the area to be protected is a space within a room and objects present within the area to be protected include ceiling surfaces, wall surfaces or floor surfaces.

3. A microwave sensor comprising:
    an RF module operable to transmit a plurality of microwaves of different frequency toward an area intended to be protected and to receive respective reflected microwaves from an object to be detected if present within the area to be protected using transmitting and receiving antennas;
    a signal processing unit operable to process signals from said RF module; and
    a distance measuring arithmetic unit connected with said signal processing unit operable to measure the distance to the object to be detected based on phase difference between or among the reflected microwaves, said distance measuring arithmetic unit comprising:
        a storage means for storing in advance actual correlation data of actual correlations between or among distances to objects to be detected and phase differences of respective reflected waves that have been established based on microwave reflection by objects present within the area to be protected other than the objects to be detected; and
        a measuring means for measuring distances to objects to be detected based on the actual correlation data stored by said storage means.

4. The microwave sensor of claim 3, wherein the area to be protected is a space within a room and objects present within the area to be protected include ceiling surfaces, wall surfaces or floor surfaces.

* * * * *